(12) United States Patent
Hardt et al.

(10) Patent No.: US 7,790,195 B2
(45) Date of Patent: Sep. 7, 2010

(54) METHOD FOR PRODUCING ADHESIVE BLANKS FROM AN ENDLESS BAND AND BLANKS OBTAINED ACCORDING TO SAID METHOD

(75) Inventors: Frank Hardt, Hausen (DE); Paul Genich, Andernach (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 1199 days.

(21) Appl. No.: 10/670,046

(22) Filed: Sep. 24, 2003

(65) Prior Publication Data
US 2004/0057984 A1 Mar. 25, 2004

Related U.S. Application Data

(63) Continuation of application No. 09/763,268, filed as application No. PCT/EP99/05562 on Aug. 2, 1999, now Pat. No. 6,649,011.

(30) Foreign Application Priority Data
Aug. 20, 1998 (DE) ................................. 198 37 764

(51) Int. Cl.
*A61L 15/16* (2006.01)
*B32B 7/12* (2006.01)
(52) U.S. Cl. ........................ 424/447; 424/448; 424/449; 428/343; 428/40.1; 428/41.7; 428/41.8
(58) Field of Classification Search ................. 424/448, 424/447, 449; 156/267, 268, 269, 270; 428/511, 428/40.1
See application file for complete search history.

(56) References Cited

U.S. PATENT DOCUMENTS

| 3,665,918 | A | * | 5/1972 | Lindquist et al. ............... 602/75 |
| 4,063,352 | A | | 12/1977 | Bevilacqua |
| 4,333,781 | A | | 6/1982 | Meulenberg |
| 4,393,048 | A | * | 7/1983 | Mason et al. ................ 424/619 |

(Continued)

FOREIGN PATENT DOCUMENTS

DE 196 41 094 C1 6/1997

(Continued)

*Primary Examiner*—Callie E Shosho
*Assistant Examiner*—Anish Desai
(74) *Attorney, Agent, or Firm*—D. Peter Hochberg; Sean F. Mellino; Daniel J. Smola

(57) ABSTRACT

The invention relates to a method of producing adhesive die-cut articles with internal cut-outs 3 from an endless web 1, the web having a carrier layer 4, at least one adhesive layer 5 and, if appropriate, a matrix layer 6, and to a die-cut article produced by the method. In order to produce a die-cut article with an internal cut-out 3 whilst avoiding the use of a hollow punch, the contour 17 of the internal cut-out 3 and the external contour 10 of the respective die-cut article are die-cut out of the adhesive layer 5 and, if appropriate, the matrix layer 6 one after another, the external contour 10 not having any common point with the die-cutting line of the internal cut-out 3, the carrier layer 4 with the die-cutting residues from the internal cut-out 3 being pulled off over a pull-off edge, and the remaining web being transferred to a protective film 8.

12 Claims, 2 Drawing Sheets

U.S. PATENT DOCUMENTS

| | | | |
|---|---|---|---|
| 4,415,124 A * | 11/1983 | Carduck et al. | 244/28 |
| 4,475,969 A | 10/1984 | Reed | |
| 4,650,817 A * | 3/1987 | Allen et al. | 523/105 |
| 4,699,679 A | 10/1987 | Cartmell et al. | |
| 4,746,394 A | 5/1988 | Sueta et al. | |
| 4,853,063 A | 8/1989 | Basgil et al. | |
| 5,232,702 A * | 8/1993 | Pfister et al. | 424/448 |
| 5,244,677 A | 9/1993 | Kreckel et al. | |
| 5,716,636 A * | 2/1998 | Horstmann et al. | 424/448 |
| 6,076,002 A | 6/2000 | Cartmell et al. | |

FOREIGN PATENT DOCUMENTS

| | | |
|---|---|---|
| DE | 42 32 279 C1 | 6/1998 |
| DE | 195 47 691 C1 | 6/1998 |
| DE | 196 50 329 A1 | 6/1998 |
| GB | 532018 | 1/1941 |
| GB | 865165 | 4/1961 |
| GB | 2 019 807 A | 11/1979 |
| GB | 2 218 682 A | 11/1989 |
| WO | WO 97/14126 | 4/1997 |

* cited by examiner

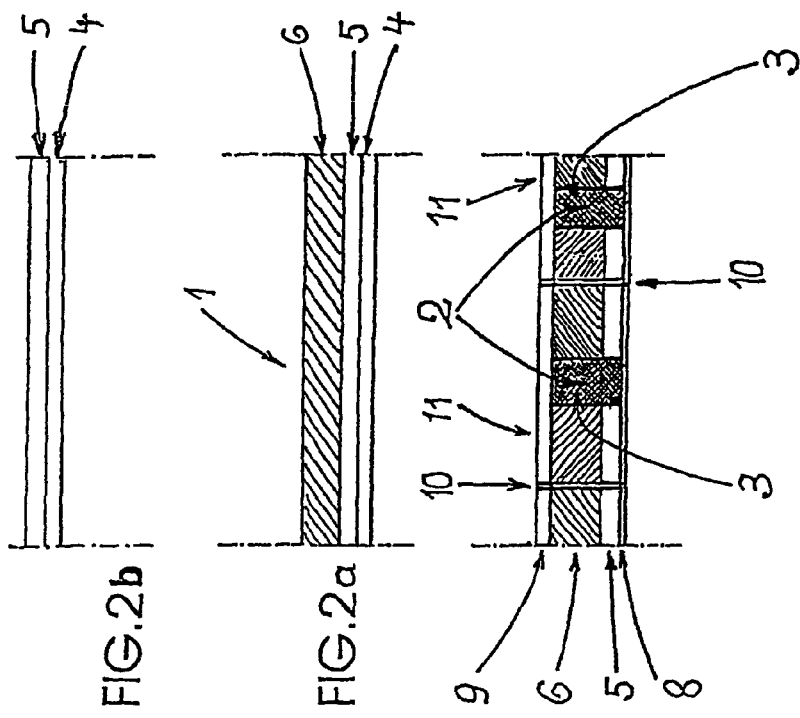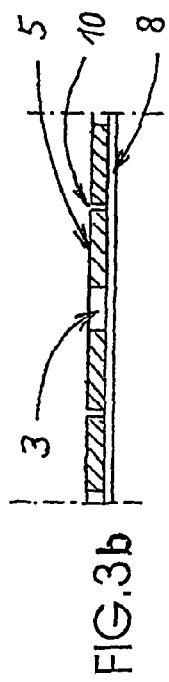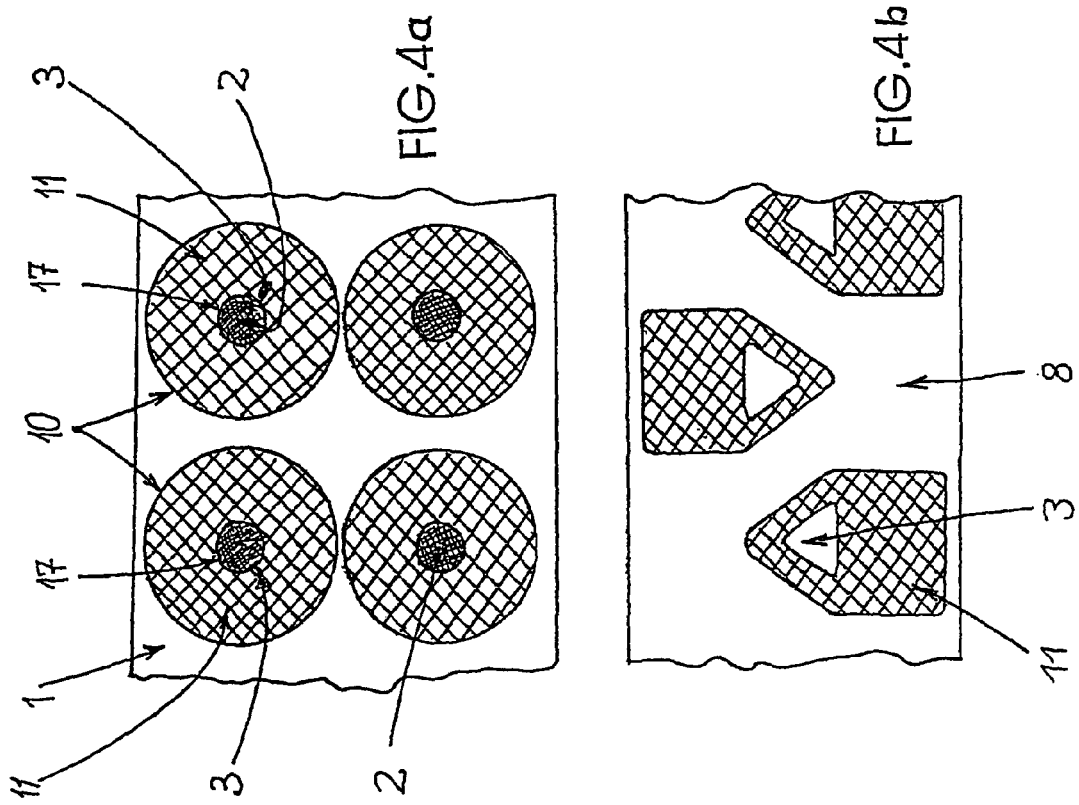

METHOD FOR PRODUCING ADHESIVE BLANKS FROM AN ENDLESS BAND AND BLANKS OBTAINED ACCORDING TO SAID METHOD

CROSS REFERENCE TO RELATED APPLICATIONS

This application is a continuation application of application Ser. No. 09/763,268, filed Apr. 2, 2001 (now U.S. Pat. No. 6,649,011, registered on Nov. 18, 2003,which is the National Stage of International Application No. PCT/EP99/05562 filed Aug. 2, 1999.

BACKGROUND OF THE INVENTION

1. Field of the Invention

The invention relates to a method of producing adhesive die-cut articles from an endless web, having at least one internal cut-out which may contain a filler material, the web having a carrier layer with at least one adhesive layer. The adhesive die-cut articles can be single-sided or double-sided adhesive sealing rings or labels provided with holes. They may also be die-cut articles in the manner of the products obtainable from Beiersdorf under the name "Power-Strips", which are additionally provided with a cut-out.

2. Description of the Prior Art

According to the prior art, appropriately shaped cut-outs are introduced into such objects, to be produced from web material, by means of a so-called hollow punch (also referred to as a complete tool). The material stamped out in the process is forced upwards in the punch. After the cut-out has been stamped out many times, it is necessary to free the material-filled punch mechanically of the stamped-out material. This entails interruptions to the continuous execution of a process. A further disadvantage is the fact that such a complete tool is a mechanically sophisticated device, which is therefore quite susceptible to faults and also expensive.

The adhesive die-cut articles can preferably be locally, regionally or systemically acting plasters with a backing layer, an adhesive layer and a reservoir of active ingredient which, until they are applied, are provided with a detachable protective layer.

Forms of medication to be applied to the skin and having the appearance of traditional plasters are known, containing medicaments which are to be discharged to the skin and, for example, are known as corn plasters. Such a system can contain one or more medicaments.

SUMMARY OF THE INVENTION

The invention is therefore based on the object of providing a method which permits the production of adhesive die-cut articles with an internal cut-out, that is, a "hole", from an endless web, whilst avoiding the use of a hollow punch.

In addition, the invention is based on the object of providing adhesive die-cut articles with an internal cut-out. A further object of the invention is to provide adhesive die-cut articles in the form of plasters which contain active ingredient and have an internal cut-out filled with filler material.

BRIEF DESCRIPTION OF THE DRAWINGS

The invention may take physical form in certain parts and arrangement of parts, a preferred embodiment of which will be described in detail in the specification and illustrated in the accompanying drawings which form a part hereof, and wherein:

FIG. 2a shows, in a section in the plane II-II, the endless web 1 composed of the carrier layer 4, the adhesive layer 5 and the matrix layer 6;

FIG. 2b shows a web 1 consisting of carrier film 4 and adhesive layer 5;

FIG. 3a shows, in a section in the plane III-III, the structure of the adhesive die-cut articles 11 after the die-cutting of the contours 17 of the internal cut-outs 3 and of the external contours 10, and after the filling of the internal cut-outs 3 with filler material 2 and after laminating a covering film 9 on;

FIG. 3b shows a die-cut article, consisting of an adhesive layer 5 and containing the internal cut-out 3, on the second carrier film 8, without any filler material;

FIG. 4a shows, in plan view, die-cut articles 11 within the external contours 10, with die-cutting contours 17 of the internal cut-outs 3 and the filler material 2 contained in the internal cut-outs 3. The die-cut articles 11 are still located within the endless web 1, before being separated;

FIG. 4b shows a plan view of adhesive die-cut articles 11 in which the internal cut-out 3 is not filled;

DETAILED DESCRIPTION OF THE PREFERRED EMBODIMENT

Figure 1:
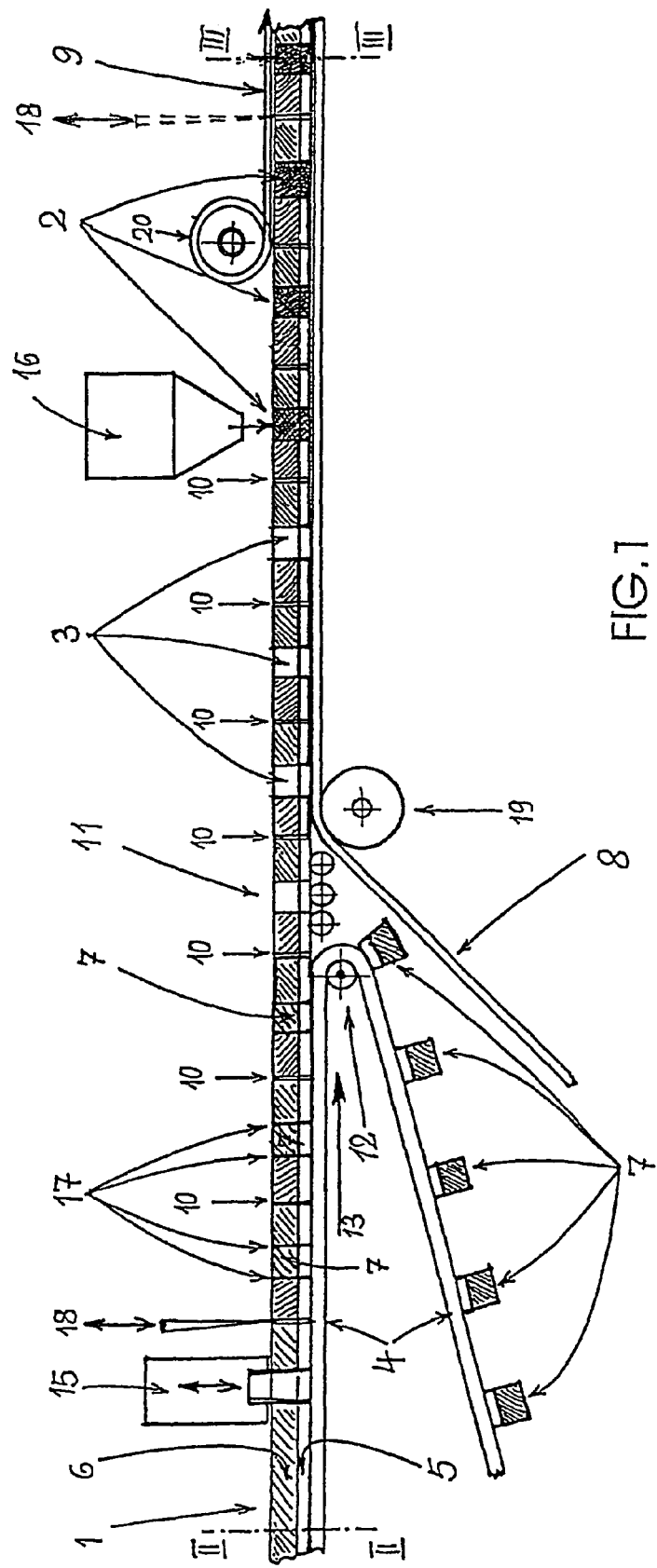
FIG. 1 shows the schematic diagram of an apparatus for implementing the method of producing adhesive die-cut articles from an endless web.

The object is achieved by a method of producing adhesive die-cut articles 11 with internal cut-outs 3 from an endless web 1, the web having a carrier layer 4 and at least one adhesive layer 5, which, according to the invention, is characterized by:

a) die-cutting the contour 17 of the internal cut-out 3 from an adhesive layer 5 and, if appropriate, from a matrix layer 6, but the carrier layer 4 not being punched through, b) die-cutting the external contour of the adhesive die-cut articles 11 from the adhesive layer 5 and, if appropriate, from the matrix layer 6 this external contour 10 of the adhesive die-cut article not having any common point with the contour 17 of the internal cut-out 3, c) deflecting the carrier layer 4 over a pull-off edge, cut-out die-cutting residues 7 of the internal cut-out being pulled off together with the unsevered carrier layer 4, d) transferring the web, freed from the carrier layer 4 and cut-out die-cutting residues 7 of the internal cut-out, or transferring the individual die-cut articles, to a protective film 8.

In this case, instead of the pull-off edge 12, a pull-off roller can also be used, which constitutes a technical equivalent. For the purpose of clarification: the cut-out die-cutting residues 7 constitute the material which, after it has been removed from the endless web 1, leave behind the internal cut-outs 3, that is, the holes, in the said web.

Further steps in the production of the plaster which contains active ingredient and is filled with filler material are:

e) filling the internal cut-out 3 with filler material 2 and laminating on a covering film 9, f) die-cutting the contour of the external plaster shape, separating the die-cut articles and stripping off the die-cutting residues.

The production method according to the invention is surprisingly uncomplicated, can be carried out without so-called hollow punches and is consequently extremely cost-effective.

One configuration of the method provides for the steps to be carried out in the sequence a) to d), if appropriate as far as f). However, differing from this, it can also be carried out in the sequence b), a), c), d), if appropriate additionally e) and f).

A further simplification is that the steps a) and b) are carried out simultaneously with each other, for example using a reciprocating punch or a cutting roll. These die-cutting tools then have a surface structure with cutting edges which have the external contour of the die-cut articles and the contour of the internal cut-out.

Finally, the operations can be carried out in the sequence a), c), d), b), if appropriate in addition e) and f).

The steps a) to d) can be carried out simultaneously, so that the method proceeds continuously at constant or variable speed. However, the method can also proceed discontinuously, specifically if the use of a reciprocating punch makes it necessary to stop the endless web 1. Preference is given to such a discontinuous method if the additional step e) is relatively time-consuming.

A further advantageous variant of the method is characterized in that the internal cut-out 3 in the adhesive layer 5 is die-cut through the matrix layer 6 and together with the latter.

The geometric shape of the internal cut-out 3 is unimportant. Preference is given to a circular shape. The important fact is that the thickness of the adhesive layer 5 and, if appropriate, of the matrix layer 6 are together less than the maximum extent of the internal cut-out 3 in the longitudinal and/or transverse direction.

An adhesive die-cut article produced by the method is characterized by:
  a) an adhesive layer 5 with an internal cut-out 3 and
  b) a redetachable protective film 8 which covers the adhesive layer 5 and the internal cut-out 3.

In addition, this adhesive die-cut article can have a matrix layer 6. This matrix layer can have an internal cut-out which is congruent with (has an identical two-dimensional shape to) the internal cut-out 3 in the adhesive layer 5.

The adhesive die-cut article can have a covering layer 9 adhering to the adhesive layer 5 or to the matrix layer 6 located above the latter. The internal cut-out 3 can, if appropriate, be filled with a filler material 2, which is preferably a compound containing an active ingredient.

Filler materials 2 considered are flowable or pourable preparations, that is to say liquid, semi-solid, gel-like, pasty, powdery or fusible materials or mixtures. The ingredients considered are, for example, topically (local and/or regionally) and/or systemically active pharmaceutical active ingredients, including salicylic acid, lactic acid, 5-fluoruracil, capsaicin, acetyl-salicylic acid, nonoic acid vanillyl amide, etc.

Suitable materials for the adhesive layer 5 are natural or synthetic polymers with contact-adhesive properties, which are known to those skilled in the art, for example polyacrylates, polyisobutylenes, silicones, rubber, SIS block copolymers, etc. If necessary, the adhesiveness must be matched to the requirements by the addition of adhesive resins ("tackyfiers").

Natural and synthetic polymers are likewise preferably considered for the matrix layer 6, such as polyacrylates, polyethylenes, polypropylenes, polybutylenes, polyurethanes, poly-1-butenes, polyisobutene, rubbers, silicon rubbers, cellulose, chemical pulp, paper, cotton, acetylcellulose, celluloid, viscose, polyacrylonitrile, polyvinyl alcohol, polyvinyl acetate, polyvinyl ether, ethylene-vinyl acetate copolymers (EVA) and the like. These materials, and consequently the matrix layer 6, are non-adhesive. They may be present as a compacted material, foam, fabric, porous sheet, nonwoven fabric, etc.

The method and the apparatus provided for implementing it are uncomplicated, comprehensible and surprisingly effective in functional terms. To this extent, the invention achieves the object set at the beginning in an optimum way.

Further details, features and advantages of the invention emerge from the following exemplary embodiments and the drawings shown.

EXAMPLE 1

Production of a Filled Die-Cut Article

During the continuous production of the adhesive die-cut articles 11 from an endless web 1, the latter is first moved in the direction of the arrow 13 into a die-cutting station 15, in which the contours 17 of the internal cut-outs 3 from at least the adhesive layer 5 are punched through, but without the carrier layer 4 being punched through at the same time. In the example shown, there is a further, optional layer, namely the matrix layer 6, on the adhesive layer 5. In the present example, both the matrix layer 6 and the adhesive layer 5 are punched through in the die-cutting station 15, but the cut-out die-cutting residue 7, that is, the "die-cutting core", initially still remaining within the contour 17 of the internal cut-out 3. Suitable die-cutting stations 15 are either a reciprocating punch, which permits a procedure with the web being stopped, or a rotating cutting roll, which permits a variable or constant web speed without the web being stopped. A high-energy laser beam, which moves over the contour 17 of the internal cut-out 3, can likewise carry out the technical function of the die-cutting station 15.

During further transport in the direction of the arrow 13, the external contour 10 of the die-cut articles 11 is then cut out of the matrix layer 6 and the adhesive layer 5 in the second cutting station 18, the external contour 10 of the said layers not having any common point with the contour 17 of the internal cut-out 3. A die-cutting grid which may be produced in the process is "stripped off". The previously die-cut endless web 1 then reaches the pull-off edge 12, at which the carrier layer 4 which has not been stamped through is pulled off together with the cut-out die-cutting residues 7.

The die-cut articles prepared in this way are immediately subsequently transferred, by a roller (19), to a protective film 8, the underside of the adhesive layer 5 being covered by the protective film 8.

During further transport of the die-cut-contour die-cut articles with internal cut-outs 3 still open (that is to say not covered and not filled), these reach a position underneath the filling station 16, which in each case puts a meterable portion of filler material 2 into the internal cut-outs 3 which have until now been open. After that, during further transport, a covering film 9 is laminated on to the die-cut articles from above in a laminating station 20.

EXAMPLE 2

Production of a Filled Die-Cut Article

As Example 1, but the die-cutting of the external contour 10 of the adhesive die-cut article 11 is carried out after the filler material 2 has been put in, that is to say the second cutting station 18 (shown dashed in FIG. 1) is located downstream of the filling station 16 and laminating station 20.

EXAMPLE 3

Production of an Unfilled Die-Cut Article

As Example 1, but the die-cutting of the contour 17 of the internal cut-out 3 and of the external contour 10 of the adhesive die-cut article are carried out simultaneously in a rotational cutting roll. Owing to the geometric shape of the external contour of the die-cut article, no die-cutting grid occurs in this case. Stripping off is therefore not necessary. During the subsequent transfer of the previously die-cut articles to the protective film 8, they are separated, since this protective film has a higher web speed than the endless web 1. No filling of the internal cut-out 3 is carried out.

EXAMPLE 4

Production of a Plaster Containing Active Ingredient

The production of a plaster containing active ingredient is carried out on a flat-bed punch which is equipped with the following units:
   second plane with die-cutting station
   laminating device
   metering station
   format die-cutter
   cross-cutter
   packaging unit with heat-sealing punch (in the case of on-line packaging)

The protective film is drawn into the machine. On a second plane, the polyethylene foam laminate is fed to a die-cutter, which cuts out the holes to be filled with active ingredient compound. The intermediate covering paper with the die-cut foam adhering to it is pulled off. The perforated foam is laminated on to the protective film and filled with active ingredient compound in the metering station. After the intermediate covering paper has been removed from the laminate, the adhesive-coated, skin-coloured polyethylene film is laminated on to the foam.

The contour of the plaster is stamped from above into this laminate, consisting of protective film, adhesive, foam with active ingredient compound, adhesive and skin-coloured polyethylene film, by means of a flat-bed punch with a strip-steel cut. Excess polyethylene film and foam are pulled off upwards, the individual plasters remaining stuck to the protective film. Following cross-cutting, the plasters are sealed in twos into packaging material.

EXAMPLE 5

Production of Adhesive Die-Cut Articles with a Rectangular Internal Cut-Out

An endless web consisting of a laminate (containing a polyethylene matrix 0.9 mm thick, a polyacrylate adhesive layer 50 µm thick and a siliconized paper carrier layer) with a width of 3 cm is led into a rotational cutting roll, which stamps out rectangular internal cut-outs 3 1.6 cm long and 6 mm wide. At the same time, this cutting roll stamps a cut at 6 cm intervals into the endless web, specifically in such a way that the internal cut-out 3 is located at the centre of the previously die-cut articles. Stripping off is not necessary, since there is no projecting edge between the die-cut articles or at their lateral boundaries. The previously die-cut articles are freed from the carrier layer 4 and the cut-out die-cutting residue 7 at a deflection roller. As they are transferred to the siliconized polyethylene terephthalate protective film 8, running at a higher speed, spacings of 1 cm are produced between the separated die-cut articles.

The invention has been described with particular emphasis on the preferred embodiments, but variations and modifications within the spirit and scope of the invention may occur to those skilled in the art to which the invention pertains.

We claim:

1. An adhesive die-cut article having an external contour comprising an adhesive layer with an internal cut-out having a contour, wherein the external contour of the adhesive die-cut article has no common point with the contour of the internal cut-out, a matrix layer having an internal cut-out which is congruent with the internal cut-out in the adhesive layer, said matrix layer being a compacted material, and a covering film covering the composite of matrix layer, adhesive layer, and internal cut-out, wherein the internal cut-out is filled with filler material containing a pharmaceutical active ingredient selected from the group consisting of salicylic acid, lactic acid, 5-fluoruracil, capsaicin, acetyl-salicylic acid, and nonoic acid vanillyl amide, and wherein the matrix layer comprises a natural or synthetic polymer selected from the group consisting of polyacrylates, polypropylenes, polybutylenes, poly-1-butenes, polyisobutene, cellulose, chemical pulp, paper, cotton, acetylcellulose, celluloid, viscose, polyacrylonitrile, polyvinylalcohol, polyvinyl acetate, polyvinyl ether and ethylene-vinyl-acetate (EVA) copolymers.

2. The adhesive die-cut article according to claim 1, further comprising a detachable protective film.

3. The adhesive die-cut article according to claim 1, wherein the internal cut-out has a circular shape.

4. The adhesive die-cut article according to claim 1, wherein the internal cut-out has a rectangular shape.

5. The adhesive die-cut article according to claim 1, wherein the thickness of the adhesive layer and of the matrix layer in sum are less than the maximum extent of the internal cut-out in longitudinal or transverse direction.

6. The adhesive die-cut article according to claim 1, wherein said filler material is selected from the group consisting of liquid, semi-solid, pasty, powdery and fusible materials and mixtures thereof 7. The adhesive die-cut article according to claim 1, wherein the adhesive layer comprises a natural or synthetic polymer selected from the group consisting of polyacrylates, polyisobutylenes, silicones, rubber and SIS block copolymers.

8. The adhesive die-cut article according to claim 1, wherein said filler material is a powdery material.

9. The adhesive die-cut article according to claim 1, wherein said filler material is a fusible material.

10. An adhesive die-cut article having an external contour comprising an adhesive layer with an internal cut-out having a contour, wherein the external contour of the adhesive die-cut article has no common point with the contour of the internal cut-out, a matrix layer having an internal cut-out which is congruent with the internal cut-out in the adhesive layer, said matrix being a compacted material, and a covering film covering the composite of the matrix layer, adhesive layer and internal cut-out, wherein the internal cut-out is filled with a filler material containing a pharmaceutical active ingredient selected from the group consisting of salicylic acid, lactic acid, 5-fluoruracil, capsaicin, acetyl-salicylic acid, and nonoic acid vanillyl amide, and wherein said filler material is a gel-like material, and wherein the matrix layer comprises a natural or synthetic polymer selected from the group consisting of polyacrylates, polypropylenes, polybutylenes, polyurethanes, poly-1-butenes, polyisobutene, rubbers, silicone rubbers, cellulose, chemical pulp, paper, cotton, acetylcellulose, celluloid, viscose, polyacrylonitrile, polyvinylalcohol, polyvinyl acetate, polyvinyl ether and ethylene-vinyl-acetate (EVA) copolymers.

11. The adhesive die-cut article according to claim 10, wherein the matrix layer comprises a natural polymer selected from the group consisting of cellulose, chemical pulp, paper and cotton.

12. The adhesive die-cut article according to claim 10, wherein the matrix layer comprises synthetic polymer selected from the group consisting of polyacrylates, polypropylenes, polybutylenes, poly-1-butenes, polyisobutene, acetylcellulose, celluloid, viscose, polyacrylonitrile, polyvinylalcohol, polyvinyl acetate, polyvinyl ether and ethylene-vinyl-acetate (EVA) copolymers.

* * * * *